United States Patent [19]
Schleupen et al.

[11] Patent Number: 5,675,069
[45] Date of Patent: Oct. 7, 1997

[54] CIRCUIT FOR PROCESSING A SIGNAL OF A MEASURING SENSOR

[75] Inventors: Richard Schleupen, Ingersheim; Hans-Dieter Schray, Markgröningen; Bernd Tepass, Ilsfeld; Walter Grote, Markgröningen, all of Germany

[73] Assignee: Robert Bosch GmbH, Stuttgart, Germany

[21] Appl. No.: 613,088

[22] Filed: Mar. 8, 1996

[30] Foreign Application Priority Data

Mar. 10, 1995 [DE] Germany .................. 195 08 560.4

[51] Int. Cl.$^6$ ............................................. G01N 7/00
[52] U.S. Cl. ................................. 73/23.32; 123/672
[58] Field of Search .......................... 73/23.32, 23.31, 73/23.2; 123/672, 676, 674; 364/424.03, 431.05

[56] References Cited

U.S. PATENT DOCUMENTS

| | | | |
|---|---|---|---|
| 4,526,147 | 7/1985 | Grob | 123/672 |
| 5,225,661 | 7/1993 | Nankee, II et al. | 123/674 |
| 5,539,638 | 7/1996 | Keeler et al. | 364/424.03 |
| 5,558,752 | 9/1996 | Wang et al. | 123/672 |
| 5,566,071 | 10/1996 | Akazaki et al. | 364/431.05 |

*Primary Examiner*—Raymond A. Nelli
*Attorney, Agent, or Firm*—Walter Ottesen

[57] ABSTRACT

The invention is directed to a circuit for processing a signal (UL) of a lambda probe having a probe signal terminal on which the signal (UL) is outputted and a probe ground terminal. The circuit includes a voltage source having a plus pole and having a minus pole connected to the probe ground terminal. A first network of passive components is connected between the plus pole and the probe signal terminal for dividing the voltage between the plus pole and the probe signal terminal in a pregiven ratio thereby providing a divided potential as a first analog signal. An analog-to-digital converter has an input and is connected to a chassis ground at a ground potential different than the ground potential at the probe ground terminal. A second network of passive components is connected to the plus pole for supplying a potential proportional to the potential on the plus pole as a second analog signal. The input of the converter is directly connected to the first network to receive the first analog signal and to the second network to receive the second analog signal thereby facilitating digital processing of the first and second analog signals in the converter.

11 Claims, 3 Drawing Sheets

CIRCUIT FOR PROCESSING A SIGNAL OF A MEASURING SENSOR

FIELD OF THE INVENTION

The invention relates to a circuit for processing the signal of a measuring sensor with the boundary conditions delineated below.

The measuring sensor supplies a signal which is greatly dependent on temperature and is only meaningful in the operationally warm condition. The circuit is therefore intended to make detection of operational readiness possible.

Furthermore, differences in ground potential can occur between the measuring sensor and a processing unit for further processing. These differences are intended to be eliminated by a simple difference formation. Furthermore, the signal supplied by the processing circuit is intended to be positive even when the measuring sensor signal is negative in relation to a reference potential.

In addition, the processed signal is intended to permit conclusions to be drawn about specific circuit faults, for example, a short circuit to ground or a short circuit of the measuring sensor signal line to battery voltage.

BACKGROUND OF THE INVENTION

An exhaust-gas probe, which is subjected to a potential, such as is used for controlling the mixture composition for an internal combustion engine in motor vehicles, represents a typical exemplary application for the processing circuit of the invention.

A processing circuit used in this context is disclosed, for example, in U.S. Pat. No. 4,526,147 which is incorporated herein by reference. The circuit used there satisfies the above-specified conditions, inter alia, with the aid of active components such as operational amplifiers.

SUMMARY OF THE INVENTION

It is an object of the invention to provide a processing circuit made up of passive components which leads to a reduction of the size of the circuit and the cost associated therewith without a reduction in accuracy when compared with existing active circuits.

The circuit of the invention is for processing a signal (UL) of a lambda probe having a probe signal terminal on which said signal (UL) is outputted and a probe ground terminal. The circuit includes: a voltage source having a plus pole and having a minus pole connected to the probe ground terminal; a first network of passive components connected between the plus pole and the probe signal terminal for dividing the voltage between the plus pole and the probe signal terminal in a pregiven ratio thereby providing a divided potential as a first analog signal; an analog-to-digital converter having input means and being connected to a chassis ground at a ground potential different than the ground potential at the probe ground terminal; a second network of passive components connected to the plus pole for supplying a potential proportional to the potential on the plus pole as a second analog signal; and, the input means of the converter being directly connected to the first network to receive the first analog signal and to the second network to receive the second analog signal thereby facilitating digital processing of the first and second analog signals in the converter.

In contrast to known solutions, the circuit according to the invention has comparatively fewer and largely passive components thereby affording advantages with respect to cost and reliability of the circuit.

BRIEF DESCRIPTION OF THE DRAWINGS

The invention will now be described with reference to the drawings wherein.

DESCRIPTION OF THE PREFERRED EMBODIMENTS OF THE INVENTION

Figure 1:
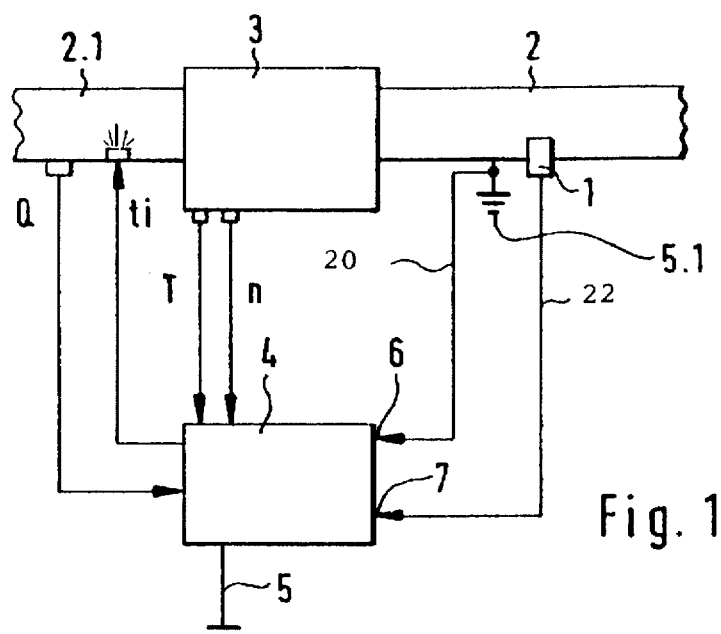
FIG. 1 is a schematic of a control arrangement for an internal combustion engine which is exemplary of a context wherein the invention is used.

FIG. 1 shows an exhaust-gas probe 1 in the exhaust-gas pipe 2 of an internal combustion engine 3 having an intake manifold 2.1. Various input signals are supplied to the control apparatus 4, for example, signals representing: load Q, engine speed (n) and temperature T of the engine as well as a signal representing the ground potential UM at the location of the exhaust-gas probe and a signal UL from the exhaust-gas probe. On the basis of these signals, the control apparatus forms output signals ti, et cetera, to control or regulate functions of the internal combustion engine such as ignition, mixture formation, et cetera. Reference numeral 5 identifies a reference ground potential which, in the case of so-called grounded body designs, corresponds to the potential of the chassis. Reference numeral 5.1 (FIG. 2) identifies the engine ground.

Because of electric currents flowing between the engine and the chassis, a ground potential 5.1, coupled to the engine, exhibits a fluctuating ground offset potential UM with respect to the reference ground potential (chassis ground) 5. Such currents flow, for example, in conjunction with the ignition, the injection valve control, starting the engine or charging the vehicle battery. In the embodiment shown, the ground offset potential UM refers to the location at which the exhaust-gas probe 1 is mounted in the exhaust-gas pipe 2. The potential UM at the ground connection of the probe is transmitted via line 20 to a terminal 6 of the control apparatus 4, while the actual signal potential UL is transmitted, via the line 22 to a terminal 7 of the control apparatus.

Figure 2:
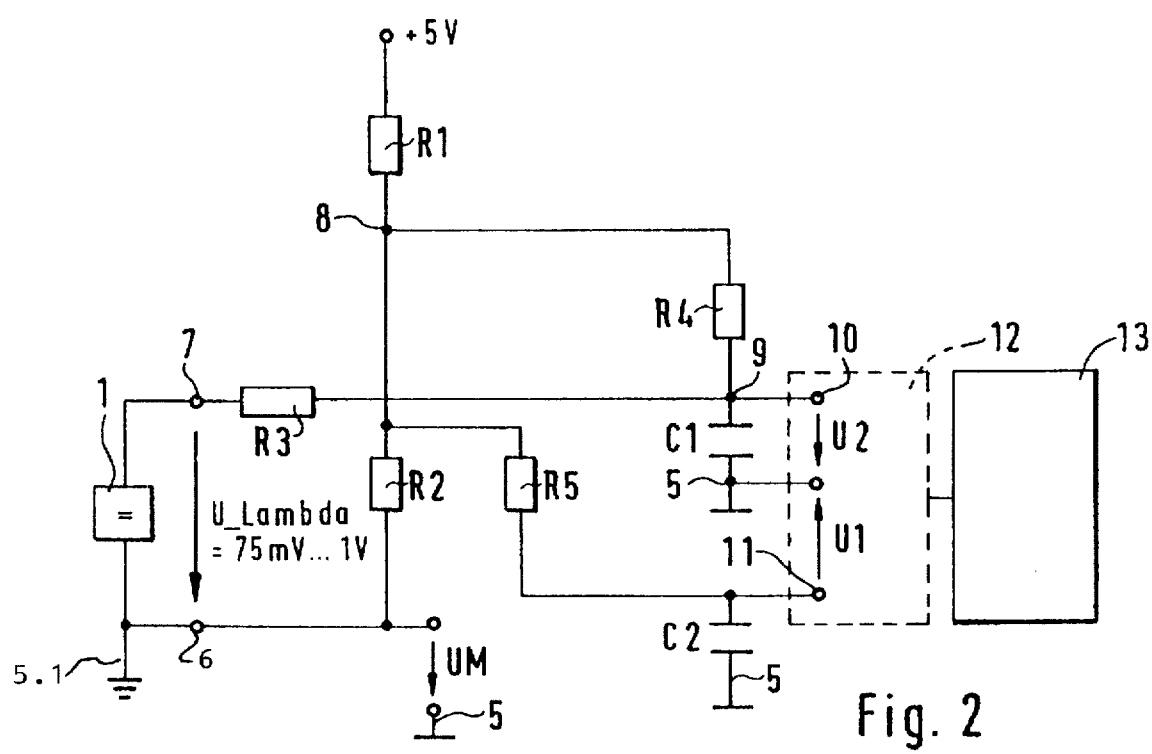
FIG. 2 is a schematic of an embodiment of a processing circuit according to the invention.

FIG. 2 shows an exemplary embodiment of the network according to the invention. The point 8 of the circuit corresponds to the positive terminal of a voltage source and is defined by the center tap of a voltage divider between a supply voltage V (for example 5V) and the ground potential 5.1 of the exhaust-gas probe 1. The voltage divider is defined by the resistors (R1, R2). This positive terminal 8 has a potential which lies, for example, at about 450 mV above UM.

A voltage divider is connected to this positive terminal 8 and is defined by a series circuit of the resistors R3 and R4. This voltage divider is connected via terminal 7 to the signal potential UL of the exhaust-gas probe 1. Resistors R3 and R4 thus form means, realized as a series circuit of ohmic resistors, for dividing a potential difference. The resistors R3 and R4 are so dimensioned that their total resistance corresponds to the internal resistance of the lambda probe when the operating temperature of the lambda probe is reached (10 to 100 kiloohms). The value of the resistors (R3, R4) of the series circuit corresponds to half the total resistance of the series circuit. The center tap 9 of this voltage divider series circuit is applied to a first input 10 of a digitizing means 12 (analog-to-digital converter), which is capacitively connected to the reference ground potential (chassis ground) 5 via a capacitor C1.

The voltage between the input 10 and the reference ground potential 5 is identified by U2. The potential at the positive terminal 8 is applied to a second input 11 of the digitizing means via a resistor R5. Resistor R5 is advantageously dimensioned such that its resistance corresponds to the resistance of a parallel circuit of the resistors R3 and R4. Input 11 is capacitively connected to the reference ground potential 5 via capacitor C2. The voltage between the input 11 and this reference ground potential 5 is designated by U1. The digitized signal is further processed in computer 13. The computer 13 can be a separate microprocessor such as a microcontroller into which the analog-to-digital converter 12 is integrated.

The network shown satisfies the requirements initially mentioned herein for a processing circuit. Individual components in this arrangement execute a plurality of functions. For example, a counter voltage to the signal voltage UL of the exhaust-gas probe 1 is provided at the center tap 9 of the series circuit of resistors R3 and R4, and therefore makes a reliable cold/hot detection of operational readiness possible. If the resistors and capacitors are dimensioned so that R3=R4 and R1/R2=10/1 and so that the condition that R1 in parallel with R2 is significantly less than R3+R4 is satisfied, then, in the case of a hot probe (that is, a low probe internal resistance of approximately 100 Ohm), the following equation is applicable to a very good approximation for the signal UL1 (fluctuating between 75 mV and 1V) of the exhaust-gas probe:

$$UL1=2(U2)-2.1(U1)+500\ mV.$$

In other words: the signal UL1 can be calculated, in the case of a hot probe, by a simple difference formation from the voltages at the inputs 10 and 11 of the analog-to-digital converter 12. In the case of a cold exhaust-gas probe (UL2), with an internal resistance in the megaohm range, U1=U2, so that the absence of operational readiness of the exhaust-gas probe 1 can be derived from UL. In this case, a lambda substitute voltage is formed as $$UL2=(UM+500mV)/1.1.$$

In order to ensure dynamically identical relationships at the two inputs (10, 11) of the analog-to-digital converter 12 with reference to fluctuations in the ground offset UM, resistors R3 and R4 are selected such that the value of their parallel connection substantially corresponds to the value of resistor R5. In addition, the capacitor C2 is so matched to the value of resistor R5 of the connection between the positive terminal 8 of the voltage source and the input 11 of the converter 12, on the one hand, and the capacitor C1 to the resistance value of a parallel connection of the ohmic resistors (R3, R4) of the above-mentioned series circuit in such a way that, at the two inputs (10, 11) of the digitizing means, dynamically identical relationships with reference to fluctuations of the potential difference between the reference ground potential (chassis ground) and the potential of the negative terminal of the lambda probe prevail. In the case shown, both the capacitors C1 and C2 have the same value.

A RC component consisting of C2 and R5 then has the same time constant as a RC component consisting of R3 in parallel with R4 and C1, which results in the intended identical time behavior at the converter inputs. As a result of the identical time behavior, the difference signal is acquired correctly even in the case of dynamic ground offsets. Furthermore, the time interval between the two analog-to-digital conversions should be kept small in relation to the RC time constant.

Figure 3:
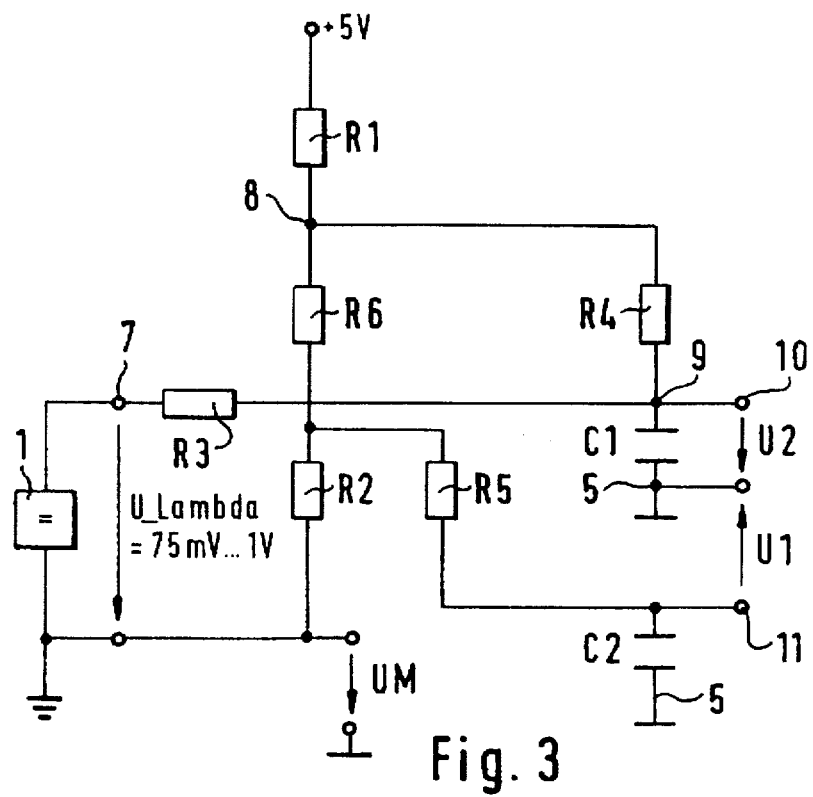
FIG. 3 is a schematic of another embodiment of the processing circuit of the invention.

The embodiment of FIG. 3 differs from that of FIG. 1 by an additional resistor R6 between the resistors R1 and R2. The sum of the resistances of resistors R2 and R6 in this case corresponds approximately to the value of the resistor R2 of FIG. 2. As a result of this change, the rule for calculating UL is simplified (provided that R1 in parallel with R2+R6 is significantly less than R4+R5) to:

$$UL1=2\times(U2-U1)$$

for a hot probe, which leads to the advantage of a shortened calculation time in the computer 13 because of the simpler algorithm.

Figure 4:
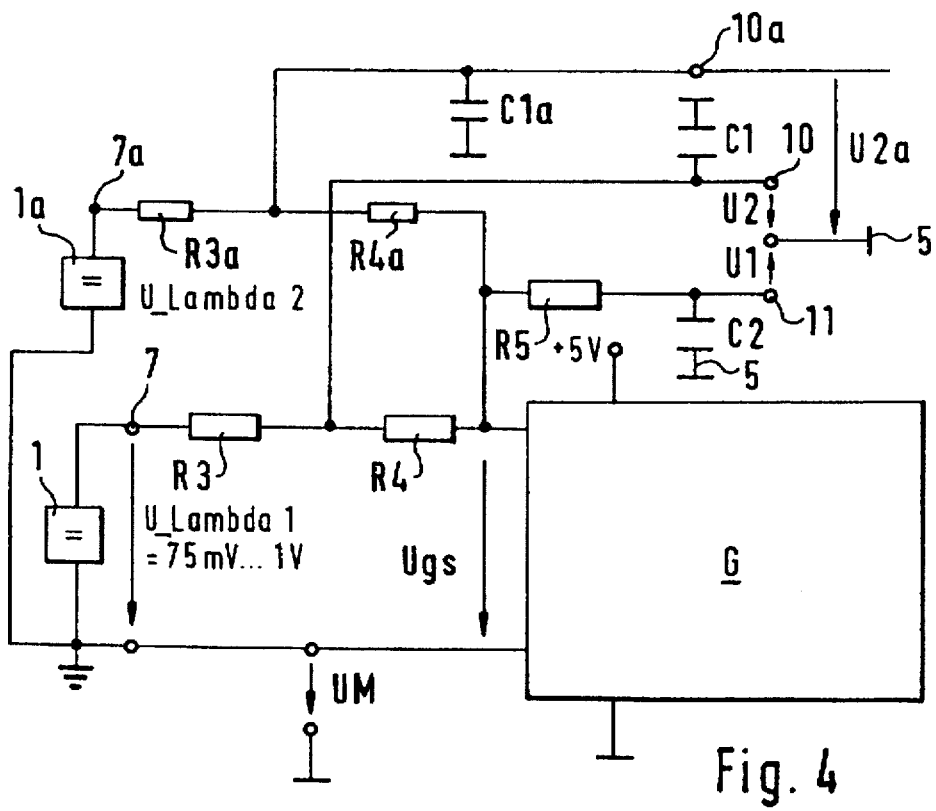
FIG. 4 is a schematic of another embodiment of the processing circuit of the invention wherein a constant voltage source is utilized; and, FIG. 5 is a schematic of still another embodiment of the processing circuit of the invention wherein a simultaneous processing of several voltages takes place via several converter inputs.

A further embodiment is shown in FIG. 4. This embodiment differs from the above embodiments in that a constant voltage source G (which is present in any case in the control apparatus) is used to provide a counter voltage UGS. The voltage UL1 of a (hot) exhaust-gas probe 1 (assuming that R3≡R4) is obtained in this exemplary embodiment from the equation:

$$UL1=2(U2-U1)+UGS.$$

An additional second exhaust-gas probe 1a in FIG. 4 shows how the system can be expanded to multiple probe systems without difficulty. The index (a) in FIG. 4 identifies the circuit path belonging to a second exhaust-gas probe 1a. The voltage U2a at the analog-to-digital converter input 10a results in a manner analogous to the voltage U2 at the analog-to-digital converter input 10. Accordingly, UL for the second (hot) exhaust-gas probe yields $$UL2=2(U3-U1)+UGS.$$

A second exhaust-gas probe is used, for example, in the case of separate lambda controllers for individual cylinder banks of a V engine.

Figure 5:
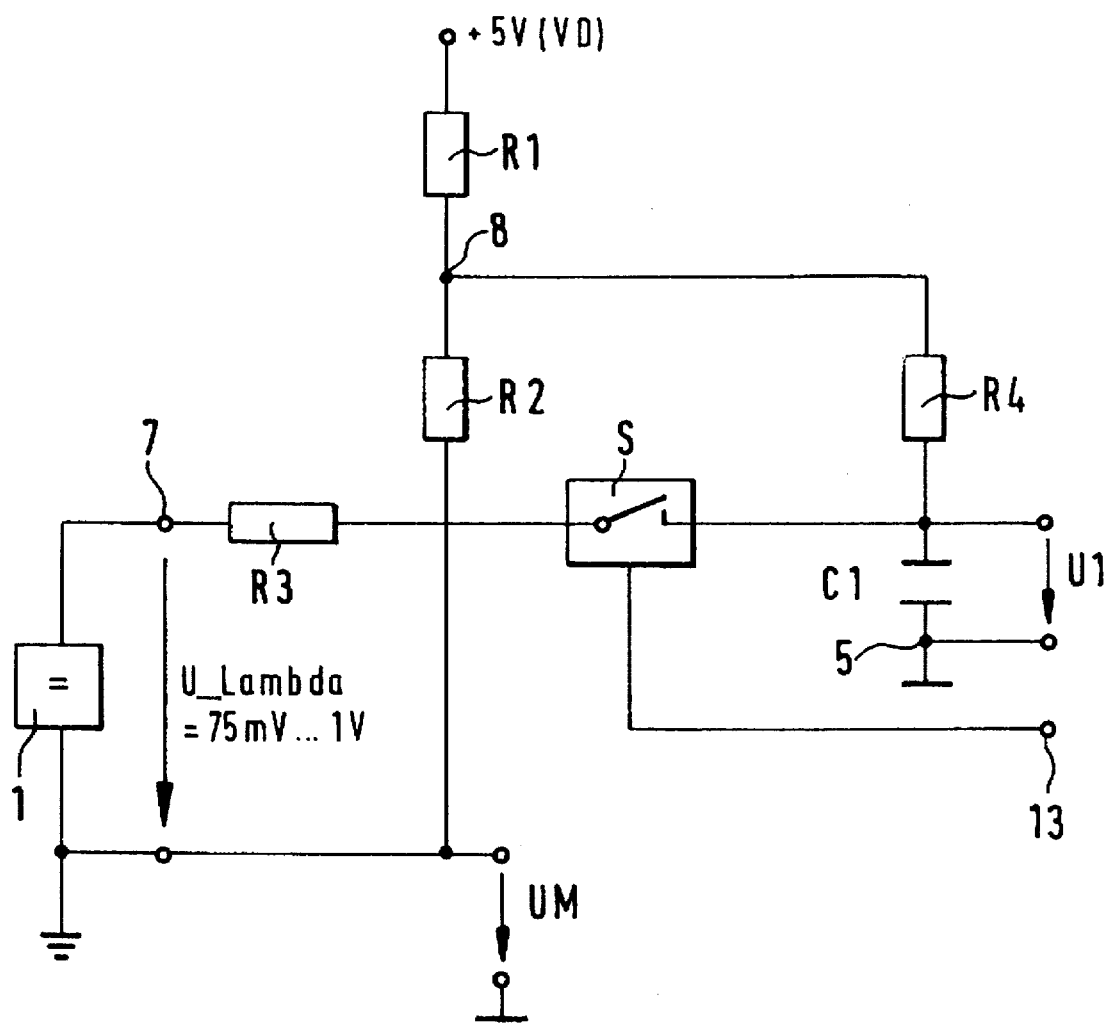

FIG. 5 shows a further embodiment of the invention, in which the simultaneous processing of the voltages (U1, U2) via several analog-to-digital converter inputs from the above embodiments is substituted by time-dependent clocked processing via a single analog-to-digital converter input. For this purpose, the switch S is opened or closed under computer control 13. When the switch S is closed, the voltage U1 from FIG. 5, as U1_closed, corresponds to the voltage U2 from FIG. 2. When the switch S is open, U1 from FIG. 5, as U1_open, corresponds to the voltage U1 from FIG. 2. If the probe is hot and the switch S is opened, assuming that R1/R2=10/1 and R1 in parallel with R2 is significantly less than R3+R4, the ground offset UM for this circuit is:

$$UM=1.1(U1\_open)-500\ mV.$$

If the switch S is closed, the lambda voltage (U1_closed) yields a value corresponding to the voltage U1 from FIG. 2.

During sampling, it is necessary to wait for the recharging time of the capacitor C1 and to take into account the various time constants.

For a hot exhaust-gas probe, UL1 in this embodiment is obtained from:

$$UL1=2(U1\_closed)-2.1(U1\_open)+500\ mV.$$

In the case of a cold probe, in analogy with FIG. 1, a lambda substitute voltage $$UL2 = (UM + 500 \, mV)/1.1$$

is formed.

It is understood that the foregoing description is that of the preferred embodiments of the invention and that various changes and modifications may be made thereto without departing from the spirit and scope of the invention as defined in the appended claims.

What is claimed is:

1. A circuit for processing a signal (UL) of a lambda probe having a probe signal terminal on which said signal (UL) is outputted and a probe ground terminal, the circuit comprising:

a voltage source having a plus pole and having a minus pole connected to said probe ground terminal;

a first network of passive components connected between said plus pole and said probe signal terminal for dividing the voltage between said plus pole and said probe signal terminal in a pregiven ratio thereby providing a divided potential as a first analog signal;

an analog-to-digital converter having input means and being connected to a chassis ground at a ground potential different than the ground potential at said probe ground terminal;

a second network of passive components connected to said plus pole for supplying a potential proportional to the potential on said plus pole as a second analog signal; and, said input means of said converter being directly connected to said first network to receive said first analog signal and to said second network to receive said second analog signal thereby facilitating digital processing of said first and second analog signals in said converter.

2. The circuit of claim 1, wherein said input means includes first and second inputs for separately receiving said first and second analog signals, respectively.

3. The circuit of claim 1, wherein said input means includes a single input; and, said first and second analog signals are shifted in time with respect to each other and are applied to said single input.

4. The circuit of claim 1, said input means being capacitively coupled to said chassis ground.

5. The circuit of claim 4, said first network including a series circuit of ohmic resistors connected to each other at a common circuit node wherefrom said first analog signal is supplied to said input means.

6. The circuit of claim 5, said series circuit having a total resistance in the range of 10 to 100 kiloohms.

7. The circuit of claim 5, said series circuit having a total resistance; said lambda probe having a predetermined internal resistance when said lambda probe reaches operating temperature and said predetermined internal resistance corresponding approximately to said total resistance.

8. The circuit of claim 6, a first one of said ohmic resistors being connected between said plus pole and said common circuit node and a second one of said ohmic resistors being connected between said probe signal terminal and said common circuit node; and, said first resistor and said second resistor each having a resistance equal to approximately half of said total resistance.

9. The circuit of claim 8, wherein said first and second resistors of said series circuit have a total parallel resistance when said first and second resistors are connected in parallel; and, said first resistor having a resistance value corresponding to said total parallel resistance.

10. The circuit of claim 8, said input means including first and second inputs; first and second capacitors connected to said first and second inputs, respectively; said capacitors both being connected to said chassis ground thereby capacitively coupling said first and second inputs to said chassis ground;

said first and second ohmic resistors conjointly defining a first resistance value corresponding to a parallel connection thereof;

said common circuit node being connected to said first input of said converter;

said second network being connected between said plus pole and said second input and having a second resistance value measured between said plus pole and said second input; and, said first capacitor being matched to said first resistance value and said second capacitor being matched to said second resistance value so that at said first and second inputs, dynamically identical relationships are present with respect to fluctuations of the potential difference between said chassis ground and said probe ground terminal.

11. The circuit of claim 10, said first and second capacitors having the same capacitance.

* * * * *